United States Patent
Dugan

(10) Patent No.: US 7,633,397 B2
(45) Date of Patent: Dec. 15, 2009

(54) DETECTION SYSTEM EMPLOYING TRAINED ANIMALS

(75) Inventor: Regina Elvira Dugan, Rockville, MD (US)

(73) Assignee: Redxdefense, LLC, Rockville, MD (US)

( * ) Notice: Subject to any disclaimer, the term of this patent is extended or adjusted under 35 U.S.C. 154(b) by 387 days.

(21) Appl. No.: 11/649,825

(22) Filed: Jan. 5, 2007

(65) Prior Publication Data

US 2008/0163671 A1    Jul. 10, 2008

(51) Int. Cl.
    *G08B 23/00*   (2006.01)
(52) U.S. Cl. .................................................. 340/573.3
(58) Field of Classification Search ............. 340/573.3, 340/539.13, 5.52, 825.69, 521; 73/23.34; 702/188
    See application file for complete search history.

(56) References Cited

U.S. PATENT DOCUMENTS

| | | | | |
|---|---|---|---|---|
| 4,967,696 | A * | 11/1990 | Tobias | 119/719 |
| 5,608,381 | A * | 3/1997 | McCarney et al. | 340/573.3 |
| 6,616,607 | B2 * | 9/2003 | Hashimoto et al. | 600/300 |
| 6,721,681 | B1 * | 4/2004 | Christian et al. | 702/178 |
| 6,979,298 | B2 | 12/2005 | Vodyanoy et al. | |
| 2006/0170541 | A1 * | 8/2006 | Tompa et al. | 340/500 |

OTHER PUBLICATIONS

Gazit et al., "A Simple System For the Remote Detection and Analysis of Sniffing in Explosives Detection Dogs", Behavior Research Methods, Instrument & Computers, vol. 35 (I), pp. 82-89, 2003.
Gazit et al., "The Role of Context Specificity in Learning: The Effects of Training Context on Explosives Detection in Dogs", Anim Cogn, vol. 8, pp. 143-150, 2005.
Svartberg et al., "Consistency of Personality Traits in Dogs", Animal Behaviour, vol. 69, pp. 283-291, 2005.
Gazit et al., "Formation of an Olfactory Search Image For Explosives Odours in Sniffer Dogs", Ethology III, pp. 669-680, 2005.
Gazit et al., "Domination of Olfaction Over Vision in Explosives Detection by Dogs", Applied Science Behaviour Science, vol. 82, pp. 65-73, 2003.
Gazit et al., "Explosives Detection by Sniffer Dogs Following Strenuous Physical Activity", Applied Animal Behaviour Science, vol. 81, pp. 149-161, 2003.

* cited by examiner

*Primary Examiner*—Phung Nguyen
(74) *Attorney, Agent, or Firm*—Diederiks & Whitelaw, PLC

(57) ABSTRACT

A detection system includes a mobile unit in the form of a trained/in-training animal controlled, either directly or indirectly, by a handler. The mobile unit carries a portable electronics package linked to a remote unit. The animal is trained to search for target odors originating from a specified object, such as drugs, weapons, chemicals, a person or the like. Once a target odor is detected, data generated by the animal, as determined through body position, biometric or other sensors provided in the portable electronics, is either stored in memory for later review or forwarded to a remote unit for immediate evaluation. In this manner, the handler is provided with confirmation that the animal has sensed a target odor, thereby increasing the overall efficacy of the detection system and reducing the possibility of incorrectly reinforcing responses that are not associated with the desired target odors.

27 Claims, 3 Drawing Sheets

DETECTION SYSTEM EMPLOYING TRAINED ANIMALS

BACKGROUND OF THE INVENTION

1. Field of the Invention

The present invention pertains to the art of detection systems and, more particularly, to a detection system that employs trained/in training animals electronically linked to a handler/analyzer.

2. Discussion of the Prior Art

The ability to rapidly and effectively detect target substances is a foundational effort of law enforcement and commercial efforts around the world. Trafficking of narcotics, other banned substances and even people is on the rise. Drugs, weapons, currency, banned foodstuffs, chemicals and/or illegal aliens are transported across national borders on a daily basis. In addition to cross border trafficking, many illegal substances are produced/grown within national borders. In the United States, the Drug Enforcement Agency (DEA), the Department of Homeland Security and other state and local authorities are in a constant battle to stem the flow and production of banned substances into and among the states.

Federal and local law enforcement agencies fight a constant battle to conserve time and resources in their efforts to find lost people and to investigate property crimes such as arson. The EPA reflects an increasing concern with the potential for people to be exposed to indoor contaminants such as molds or pesticides. Commercial enterprises provide identification and treatment of termites while hospitals provide early identification of cancers such as bladder cancer. The method used in common by all these agencies and organizations is the use of detector dogs or canines trained to identify target odors associated with banned substances, other illegal activity or substances of interest.

Because of the operational context and/or accepted custom, detector dogs are most often used in direct concert with an individual handler who is either tethered to the dog by a lead or at least in extremely close proximity to a dog working off-lead. In either case, the purpose is to put the human operator, i.e., handler, in a position to immediately control the dog, and to interpret the dog's response to olfactory stimuli. In essence, the handler is the transducer of signals from the dog. This paradigm for employing detector dogs is effective and considered best practice in many detection tasks. However, such a paradigm can also introduce problems in performance or in maintenance of proper training. Occasionally, the handler will misinterpret responses from the dog resulting in pulling the dog away when an actual detection is made or rewarding the dog when no target odor is truly present.

Equally as important, all dogs are trained by humans to perform their conditioned response to odor stimulus. Training, especially initial training, is conducted on leash, with the trainer observing the dog carefully so as to time reinforcement or reward simultaneously with the initial change in behavior by the dog. When those initial changes are not observed or are misinterpreted, the reinforcement given to the dog is inaccurate or untimely. Either result creates confusion or erroneous training for the dog, increasing the time required to train the dog, creating the opportunity for spontaneous recovery of inaccurate training and in some case causing the dog to become a training failure.

Based on the above, there exists a need for improvements in using canines, or other animals, as detection systems. More specifically, there exists a need for a detection system that aides a handler's/trainer's understanding and interpretation of response signals exhibited by the trained canine or other animal.

SUMMARY OF THE INVENTION

The present invention is directed to a detection system which uses the biological responses of conditioned animals, most preferably canines. In accordance with a simple form of the invention, the detection system includes a mobile unit in the form of a trained/in training canine carrying a portable electronics package. The canine is trained to search for target odors that originate from various substances such as drugs, weapons, chemicals, people and the like. Once a target odor is detected, data generated from the canine is either stored in the portable electronics package for later review or forwarded to a remote unit for immediate evaluation. In this manner, an additional level of analysis is performed to aide in evaluating the canine's response.

The portable electronics package is linked to the remote unit through a wireless interface. Preferably, the portable electronics package includes a position indication unit, a communications unit and a sensor unit. The position indicating unit is most preferably a GPS, which, in accordance with one aspect of the invention, is supplemented with an Inertial Navigation System or INS unit for increased accuracy. Alternative position indicating systems, such as RF triangulation, can also be used. The communications unit includes both a local portion for communicating with the trained/in training canine and a remote portion for communicating with the remote unit. The sensor unit preferably includes a biometric sensor that receives input from the canine. In addition, the sensor unit may also include a body position sensor. Most preferably, the sensor unit includes both the biometric sensor and body position sensor. In addition to the above, the sensor unit may also be provided with additional sensor feeds, such as video signals. In any event, the body position sensor identifies changes in the canines posture, such as sitting, laying or formation, which are indicative of a trained/in-training response to target odor. The biometric sensor identifies respiratory patterns, temperature variations and the like, which would be indicative of both trained/in-training and natural responses to target odors. The data is either stored in memory or passed to the remote unit for analysis.

The remote unit includes a controller or CPU linked to the GPS/INS unit, a communication portion and a data analysis portion which are accessed through a user interface. The controller contains software that tracks the canine through GPS/INS signals and employs various detection algorithms to perform analysis of data received from the canine through the sensor unit. The remote unit enables a system user, such as a handler, to effectively interpret data received from the trained/in training canine for an indication of the presence of a target odor. The data obtained from the sensor unit is compared against the detection algorithms to determine whether the trained/in-training canine has sensed a target odor. In accordance with one aspect of the invention, the remote unit allows the user to communicate with the canine in the event that line of sight is lost or conditions warrant. For example, when searching a warehouse, school or the like for target odors, the canine may leave the line of sight of the handler. Through the remote unit, the handler can locate and review data and communicate with the canine. Thus, not only can the handler determine whether a target odor has been located without actually seeing signals from the canine, the canine can be guided to various way points or areas to reunite with the handler. The remote unit can also be linked to a central database to download, upgrade and refine the detection algorithms and/or seek additional experience/expertise interpreting signals received from the canine.

Additional objects, features and advantages of the present invention will become more readily apparent from the following detailed description of a preferred embodiment when taken in conjunction with the drawings wherein like reference numerals refer to corresponding parts in the several views.

DETAILED DESCRIPTION OF THE PREFERRED EMBODIMENT

Figure 1:
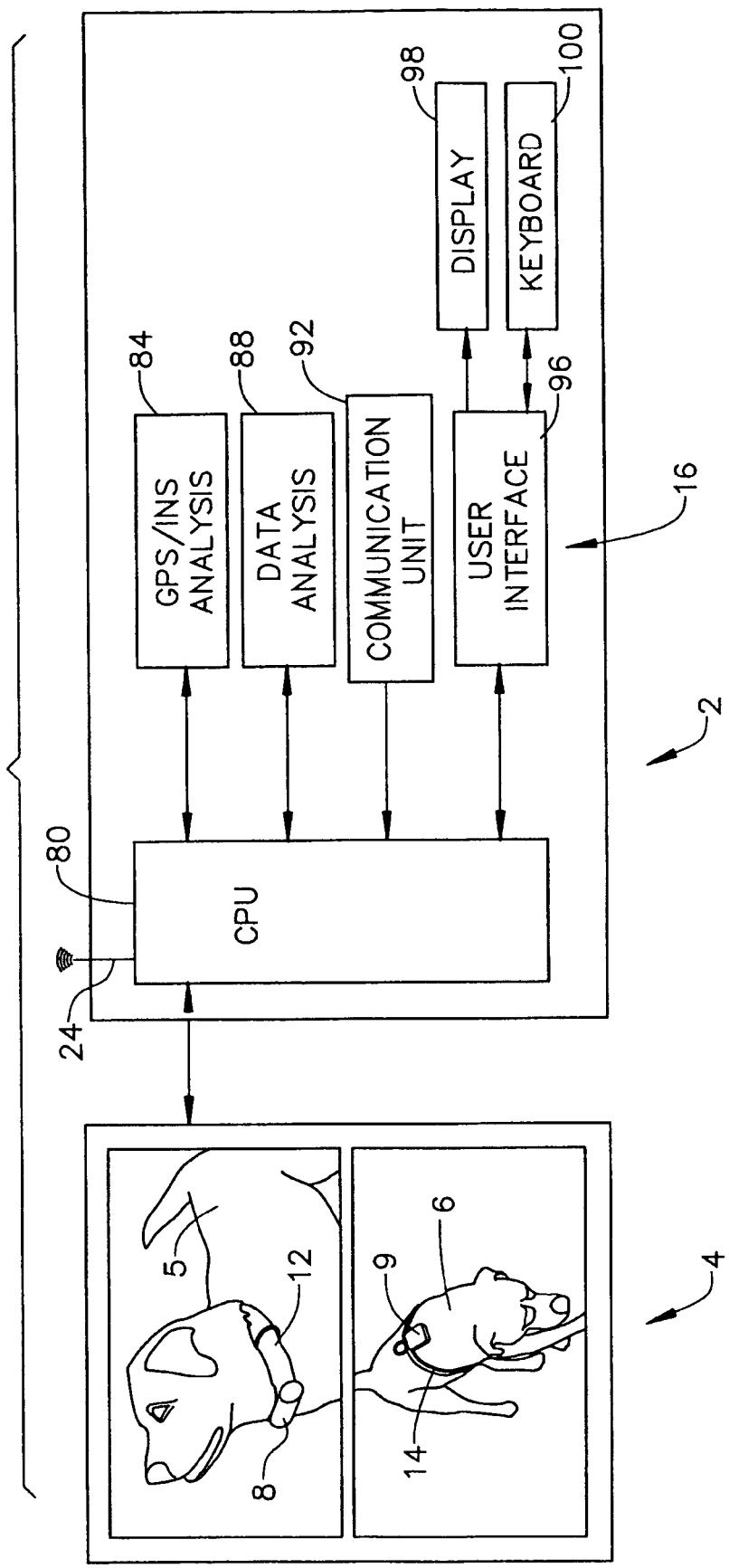
FIG. 1 illustrates a detection system constructed in accordance with the present invention.

With initial reference to FIG. 1, a detection system constructed in accordance with the present invention is generally indicated at 2. Detection system 2 includes a mobile detection unit 4 in the form of one or more trained/in training canines illustrated at 5 and 6 carrying respective portable electronics packages 8 and 9. Portable electronics packages 8 and 9 are correspondingly constructed but for the means of attachment to canines 5 and 6. That is, electronics package 8 is attached to a collar 12 on canine 5, while electronics package 9 is attached to a body harness 14 mounted to canine 6. It should be readily understood that the manner in which the package is affixed to the animal can take on various forms. In particular, various elements of the package might also be distributed in various locations so as to improve performance and/or data collection/transmission. In any case, each electronics package 8, 9 is linked to a remote unit 16. More specifically, each electronic package 8, 9 is linked to remote unit 16 through various known wireless communication protocols, with remote unit 16 receiving signals through an antenna 24. It should be readily understood that the particular manner in which signals are passed between mobile detection unit 4 and remote unit 16 can take on various forms. As will be discussed more fully below, detection system 2 enables deployment and optionally, leash independent operation of mobile detection unit 4. As will also become more fully evident below, the present invention enables a handler to track mobile detection unit 4, provide certain command capabilities in the absence of line-of-sight and/or auditory queues, and receive signals from various sensors.

Figure 2:
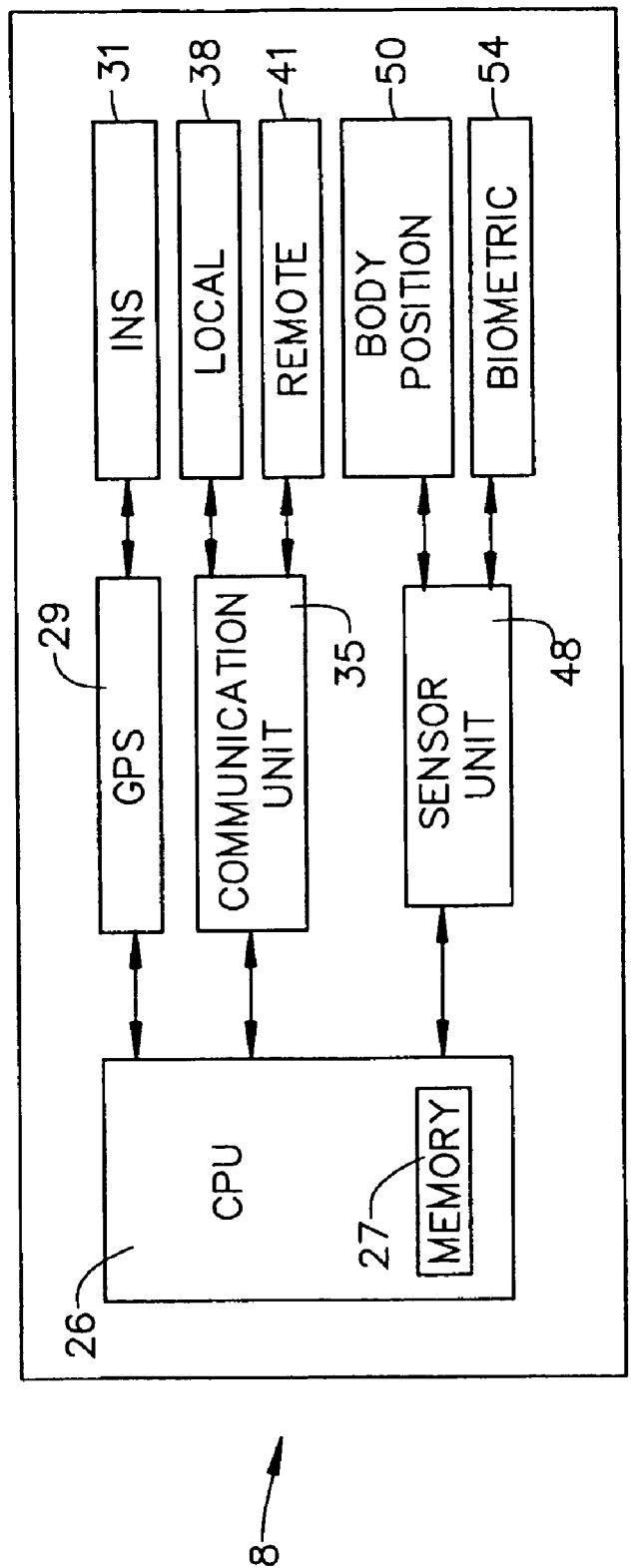
FIG. 2 illustrates a portable electronics package portion of the detection system.

At this point, a detailed description will be made of portable electronics package 8 provided on canine 5 as depicted in FIG. 2 with an understanding that electronics package 9 is correspondingly constructed. As shown, electronics package 8 includes a controller or CPU 26 is having a memory 27 and which is linked to a Global Positioning System (GPS) 29. GPS 29 is linked to an inertial navigation system (INS) 31 that is provided to supplement GPS signals. In addition, controller 26 is linked to a communications unit 35 having both a local communication element 38 and a remote communication element 41. Finally, controller 26 is also linked to a sensor unit 48 having a first or body position sensor 50 and a second or biometric sensor 54. Sensor unit 48 could also be provided with additional sensors, such as a video feed (not shown). Body position sensor 50 signals remote unit 16 whether canine 5 is standing, sitting or laying down as well as other body postures, while biometric sensor 54 provides input regarding biometric signals from canine 5, such as respiratory patterns, temperature variations and the like. As will be discussed more fully below, data received from sensors 50 and 54 is sent to remote unit 16 which employs various detection algorithms to analyze the signals received from sensor 50 and 54. The analyzed data is then reviewed by a trained handler 70 (see FIG. 3) to determine whether canine 5 actually senses the presence of a target odor or has simply made an erroneous indication. Canine 5 can be trained to detect explosives, lost people, molds, pesticides or evidence of a crime such as accelerants used to commit arson. Of course, canine 5 could be trained to detect numerous other target odors depending upon various perceived needs. Alternatively, or in addition, the data is simply stored in memory 27 and retrieved for later review. The data stored in memory 27 can also be transmitted to a central depository where the detection algorithms can be continually refined/updated. As stated above in referring to FIG. 1, electronic package 8 is connected through a wireless link to remote unit 16. Towards that end, remote unit 16 is provided with a CPU 80 that is connected to a GPS/INS analysis portion 84, a data analysis portion 88, a communication portion 92 and a user interface 96. User interface 96 includes a display 98 and a keyboard 100. In the preferred form of the invention, remote unit 16 is constituted by a handheld device, such as a PDA, Blackberry™ or the like. However, it should be readily understood that remote unit 16 could take on various other forms, such as, for example, a personal computer.

Figure 3:
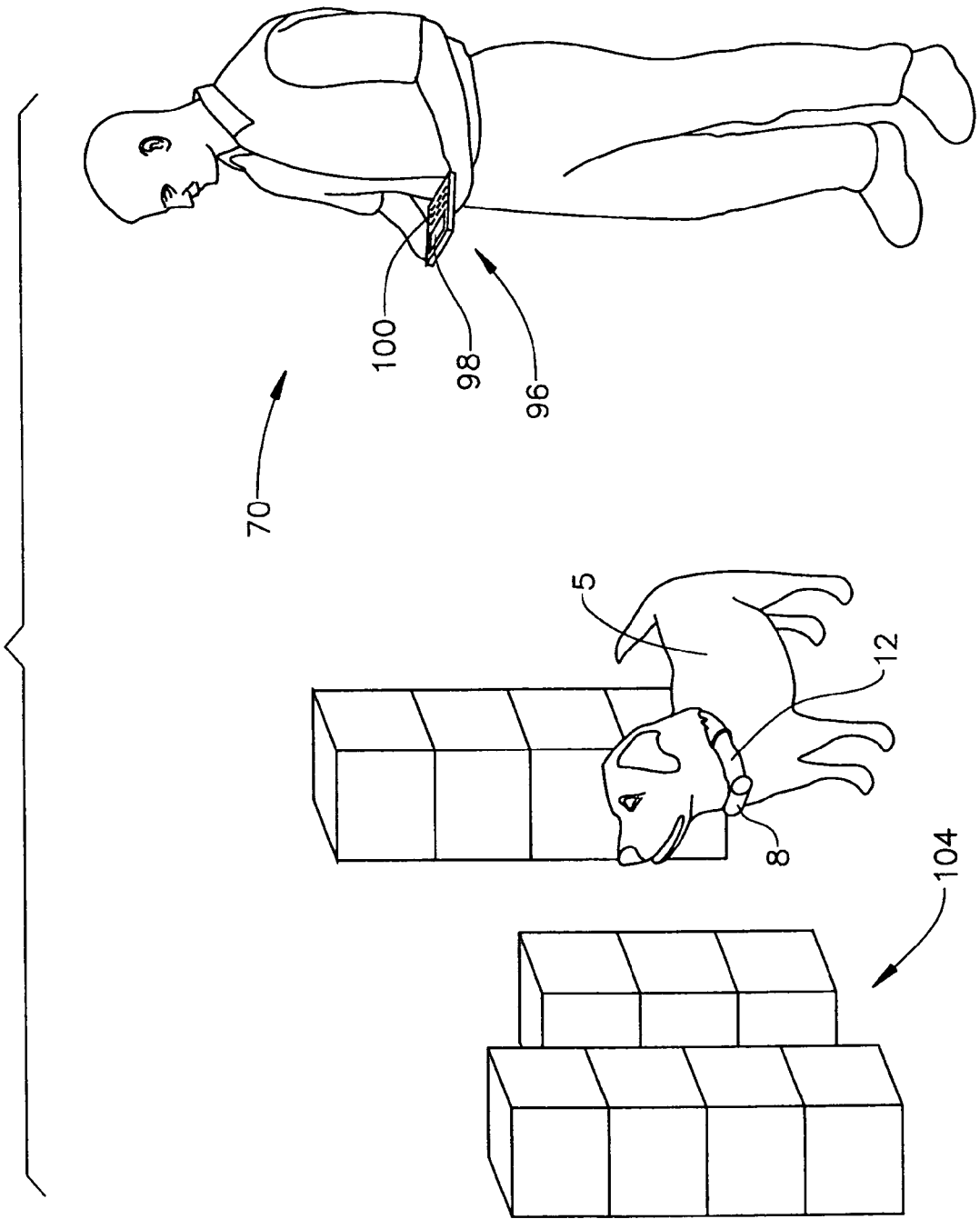
FIG. 3 illustrates a handler and remote unit associated with the present invention.

In accordance with the invention, canine 5 will predominantly undertake a search pattern within a designated area of interest or AOI, such as shown in FIG. 3, alongside handler 70. While canine 5 will typically be within line of sight of handler 70 while searching any number of areas, such as a school, warehouse, car or the like, handler 70 could lose sight of canine 5. Thus, providing handler 70 with remote unit 16 enables communication with canine 5 through a link between communication unit 92 provided in remote unit 16 and remote communication element 41 located on electronics package 8. For example, the handler can communicate through the use of a low level speaker that provides voice and/or tone commands to canine 5. Handler 70 can employ the commands to direct canine 5 to a particular area, or order canine 5 to wait, enabling handler 70 to re-establish line-of-sight contact. Moreover, handler 70 can utilize the GPS unit to geospatially locate and/or track canine 5 until line-of-sight contact is re-establish. In addition, remote unit 16 can be linked to a central database or internet web subscription service allowing handler 70 to receive additional expertise/interpretation of the signals received from canine 5.

In addition to tracking canine 5 through GPS and INS command systems and communicating through remote unit 16, handler 70 can, through sensor unit 48, determine whether canine 5 has detected a target odor. Ordinarily, once in the presence of a target odor such as from boxes 104, canine 5 may change body position and/or respond with an increased respiratory or sniff rate. For example, when in the presence of a target odor, canine 5 may become extremely active or signal through some other manner, that a target odor is present. However, on occasion, handler 70 may misinterpret signals exhibited by canine 5, or in the event that line-of-sight is lost, simply not see the signals. Therefore, body position sensor 50 can signal whether canine 5 has sat or laid down or otherwise indicated through a change in posture or behavior the presence of a target odor. Biometric sensors may provide other indicators of the presence of target odor. On other occasions, canine 5 might provide a false indication of a target odor in order to receive a treat from handler 70. Therefore, confirmatory information to increase the overall efficacy of detection system 2 is also conveyed through signals received from position sensor 50, biometric sensor 54, or other sensor inputs.

Remote unit 16 receives and stores data from sensors 50 and 54. The data is processed by pre-stored software or detection algorithms to determine whether canine 5 has had a physical or behavioral reaction to a target odor. The processed data is then reviewed by user/handler 70 to confirm signals exhibited by canine 5. Having the ability to sense and analyze the responses of canine 5 through body movement, breathing patterns and/or temperature changes, increases the overall accuracy of detection system 2. Thus, in addition to determining the posture of canine 5 through body position sensor 50, biometric sensor 54 is employed to sense respiratory or sniffing patterns, heart rate, body temperature and the like. In this manner, if handler 70 has any doubt whether canine 5 has sensed a target odor, a quick glance at remote unit 16 can provide a reliable confirmation, thereby increasing the handler's confidence that a target odor is indicated. In cases where line-of-sight contact is lost, data stored in memory 27 can be downloaded and analyzed at a later time. If a positive indication is present, personnel can go back to the position of the positive indication with the aide of simultaneously stored GPS or other positioning signals providing a reference.

At this point it should be realized that experienced dog handlers listen to their dogs for characteristic patterns of sniffing that indicate the presence of a target odor. Sniff patterns are established with the dog's active search for target odors and these patterns change based on the dog's proximity to a target odor. Trained/in training canines exhibit respiratory and distinct sniffing patterns when in the proximity of a target odor. Both a temperature differential of expired and inhaled air and a sound of sniffing are employed to interpretive sniffing patterns under various conditions. For example, maximum sniff rates reported across investigators and transduction techniques have been similar, e.g., around (3-6 Hz). Anatomical examination and visualization of inspired and expired air strongly suggests that sniffing is critical to directing odor molecules to olfactory receptors of the nose.

Based on the above, in accordance with one aspect of the invention, sensor 54 is employed to record and transmit to remote unit 16 sniffing patterns of canine 5 for analysis. In accordance with another aspect of the invention, remote communication portion 41 is employed to provide the handler with a notification signal, for example an audible signal, enabling discrimination between sniffing and non-sniffing or panting when line-of-sight contact is lost. In addition, data analysis portion 88 of remote unit 16 can be provided with a neural network that analyzes sniffing patterns to discriminate between sniffing characteristics of a purposeful search and other sniffing, respiratory or panting activity. Data analysis portion 88 can also, over time, "learn" specific physical and/or behavior responses of canine 5 in order to further increase accuracy. Data analysis portion 88 can also be linked to a remote database allowing the detection algorithms to be updated and/or refined to maintain optimal detection capability.

It should be readily apparent that the detection system constructed in accordance with the present invention more accurately enables the detection and verification of target odors found in buildings, fields, border crossings or the like so as to enable enforcement personnel to locate, confiscate and/or detain any and all contraband found. That is, by employing a mobile unit, such as a trained canine, carrying a portable electronics package that enables a user/handler to direct, control and interpret signals, the overall efficiency of detection is increased with the number of missed signals reduced and false positive signals virtually eliminated. Such a system may also provide significant benefit during training.

Although described with reference to a preferred embodiment of the invention, it should be readily understood that various changes and/or modifications can be made to the invention without departing from the spirit thereof. For example, while described as employing trained canines, other trained animals which exhibit similarly varying physical characteristics could also be employed. Instead, the invention should only be limited in accordance with the following claims.

I claim:

1. A detection system for detecting target odors through a mobile detection unit comprising:
   a portable electronics package adapted to be carried by the mobile detection unit, said portable electronics package including a sensor unit having a biometric sensor adapted to receive biometric signals emanating from the mobile detection unit that are indicative of whether the mobile unit has identified a target odor; and
   a remote unit operatively connected to the portable electronics package, said remote unit including a data analysis portion that receives and analyzes signals from the biometric sensor to determine whether the mobile detection unit has identified the target odor.

2. The detection unit according to claim 1, wherein the portable electronics package includes a position identification unit adapted to locate a position of the mobile detection unit.

3. The detection unit of claim 2, wherein the position identification unit is constituted by a GPS unit emitting signals geospatially locating a position of the mobile detection unit.

4. The detection unit according to claim 3, wherein the portable electronics package further includes an inertial navigation system.

5. The detection system according to claim 3, wherein the remote unit includes a GPS analysis portion that receives signals from the GPS unit.

6. The detection system according to claim 2, wherein the portable electronics package includes a communication unit.

7. The detection system according to claim 6, wherein the communication unit includes a local portion and a remote portion.

8. The detection unit according to claim 6, wherein the remote unit includes a communication portion operatively connected to the communication unit in the portable electronics package.

9. The detection system according to claim 1, wherein the remote unit is constituted by a hand held device.

10. The detection system according to claim 1, wherein the portable electronics package includes a memory for storing signals received from the at least one biometric sensor.

11. The detection unit of claim 1, wherein the biometric signals are sniff patterns or rates of the mobile detection unit.

12. A method of detecting target odors through the use of a mobile detection unit comprising:
    attaching a pox-table electronics package to the mobile detection unit;
    directing the mobile detection unit about an area of interest;
    determining a potential presence of a target odor;
    sensing, through the portable electronics package, a change in a physical and/or behavioral characteristic in the mobile detection unit; and analyzing the change in the physical characteristic to confirm an actual presence of the target odor.

13. The method of claim 12, further comprising: relaying signals from the portable electronics package to a remote unit.

14. The method of claim 13, further comprising: tracking the mobile detection unit through position identification unit.

15. The method of claim 14, further comprising: supplementing the GPS device with an additional positioning system.

16. The method of claim 15, wherein the GPS device is supplemented with an inertial navigation system.

17. The method of claim 13, further comprising: tracking the mobile detection unit through a GPS device located in the portable electronics package, said OPS device being linked to a GPS analysis portion in the remote unit.

18. The method of claim 13, further comprising: communicating with the mobile detection unit through the remote unit.

19. The method of claim 18, wherein communicating with the mobile detection unit includes sending tone commands from the remote unit.

20. The method of claim 18, wherein communicating with the mobile detection unit includes sending verbal commands from the remote unit.

21. The method of claim 13, further comprising: receiving auditory signals from the mobile detection unit at the remote unit.

22. The method of claim 12, further comprising: sensing a change in posture of the mobile detection unit through a body position sensor located in the portable electronics package.

23. The method of claim 12, further comprising: storing the signals of the change in the physical characteristic of the mobile detection unit in a memory provided in the portable electronics package.

24. The method of claim 23, further comprising: transmitting the stored signals to a central depository.

25. The method of claim 12, further comprising: learning the changes of the mobile detection unit that indicate the presence of the target odor in order to increase detection accuracy.

26. The method of claim 12, wherein sensing the change in the physical and/or behavioral characteristic includes determining sniff patterns or rates of the mobile detection unit.

27. A detection system for detecting target odors through a mobile detection unit comprising:
 a portable electronics package adapted to be carried by the mobile detection unit, said portable electronics package including a sensor unit having a body position sensor adapted to sense changes in body position of the mobile detection unit, said changes being indicative of whether the mobile detection unit has identified a target odor; and
 a remote unit operatively connected to the portable electronics package, said remote unit including an analysis portion that analyzes the changes in body position of the mobile detection unit to determine whether the mobile detection unit has identified a target odor.

* * * * *